(12) United States Patent
Kawabata et al.

(10) Patent No.: US 12,171,530 B2
(45) Date of Patent: Dec. 24, 2024

(54) PULSE TRANSIT TIME MEASURING APPARATUS AND BLOOD PRESSURE MEASURING APPARATUS

(71) Applicants: OMRON HEALTHCARE CO., LTD., Muko (JP); OMRON CORPORATION, Kyoto (JP)

(72) Inventors: Yasuhiro Kawabata, Kyoto (JP); Kenji Fujii, Kyoto (JP); Naomi Matsumura, Kyoto (JP); Reiji Fujita, Kyoto (JP); Akito Ito, Kyoto (JP)

(73) Assignees: OMRON HEALTHCARE CO., LTD., Muko (JP); OMRON CORPORATION, Kyoto (JP)

( * ) Notice: Subject to any disclaimer, the term of this patent is extended or adjusted under 35 U.S.C. 154(b) by 1011 days.

(21) Appl. No.: 17/009,424

(22) Filed: Sep. 1, 2020

(65) Prior Publication Data
US 2020/0397318 A1 Dec. 24, 2020

Related U.S. Application Data

(63) Continuation of application No. PCT/JP2019/006710, filed on Feb. 22, 2019.

(30) Foreign Application Priority Data

Mar. 14, 2018 (JP) .................. 2018-047031

(51) Int. Cl.
*A61B 5/021* (2006.01)
*A61B 5/00* (2006.01)
(Continued)

(52) U.S. Cl.
CPC ...... *A61B 5/02125* (2013.01); *A61B 5/02141* (2013.01); *A61B 5/02156* (2013.01);
(Continued)

(58) Field of Classification Search
None
See application file for complete search history.

(56) References Cited

U.S. PATENT DOCUMENTS

2012/0190994 A1* 7/2012 Kim ..................... A61B 5/318
600/509
2017/0035305 A1* 2/2017 Moon .................. A61B 5/6826
(Continued)

FOREIGN PATENT DOCUMENTS

GB 2367621 A 4/2002
JP H07-136136 A 5/1995
(Continued)

OTHER PUBLICATIONS

Sep. 17, 2020 International Preliminary Report on Patentability issued in International Patent Application No. PCT/JP2019/006710.
(Continued)

*Primary Examiner* — Benjamin S Melhus
(74) *Attorney, Agent, or Firm* — Oliff PLC

(57) ABSTRACT

A pulse transit time measuring apparatus according to one aspect includes a belt unit configured to be wrapped around a measurement site of a user, an electrocardiogram acquisition unit including electrodes provided at the belt unit and configured to acquire an electrocardiogram of the user by using the electrodes, a pulse wave signal acquisition unit including a pulse wave sensor provided at the belt unit, and configured to acquire a pulse wave signal representing a pulse wave of the user by using the pulse wave sensor, and a pulse transit time calculation unit configured to calculate a pulse transit time based on a time difference between a waveform characteristic point of the electrocardiogram and a waveform characteristic point of the pulse wave signal.

8 Claims, 9 Drawing Sheets

(51) Int. Cl.
A61B 5/0215      (2006.01)
A61B 5/25        (2021.01)
A61B 5/0235          (2006.01)

(52) U.S. Cl.
CPC .............. A61B 5/25 (2021.01); A61B 5/6824 (2013.01); A61B 5/683 (2013.01); A61B 5/0235 (2013.01); A61B 2562/0247 (2013.01)

(56) References Cited

U.S. PATENT DOCUMENTS

2017/0340219 A1* 11/2017 Sullivan ............. A61B 5/14551
2018/0353089 A1* 12/2018 Choi ...................... A61B 5/742

FOREIGN PATENT DOCUMENTS

| | | |
|---|---|---|
| JP | H07-313472 A | 12/1995 |
| JP | H11-188012 A | 7/1999 |
| JP | 2001-161650 A | 6/2001 |
| JP | 2014-200270 A | 10/2014 |
| JP | 5984088 B2 | 9/2016 |
| JP | 6202510 B1 | 9/2017 |
| WO | 2016/040264 A1 | 3/2016 |
| WO | 2018/043692 A1 | 3/2018 |

OTHER PUBLICATIONS

May 7, 2019 International Search Report issued in International Patent Application No. PCT/JP2019/006710.

* cited by examiner

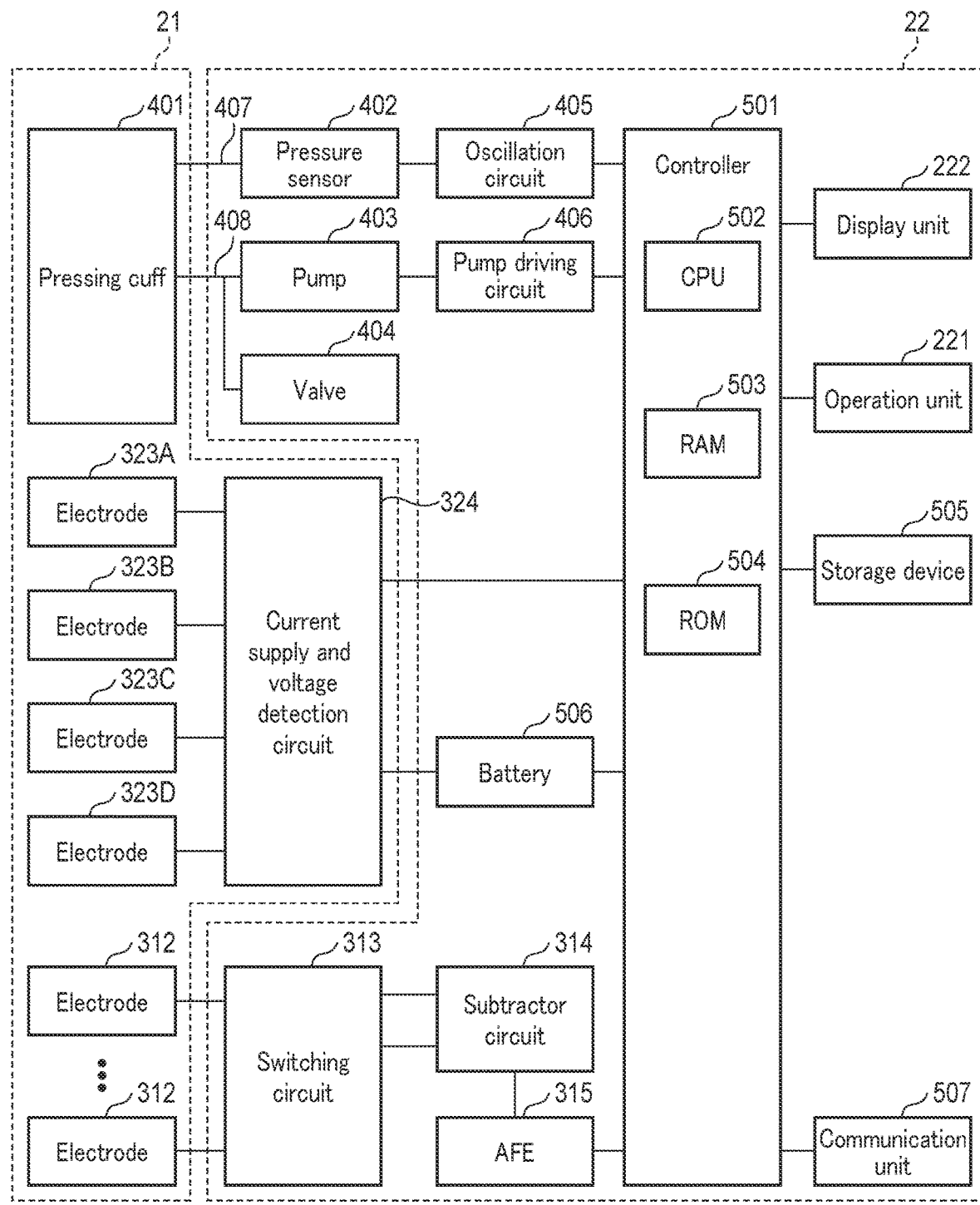
F I G. 5

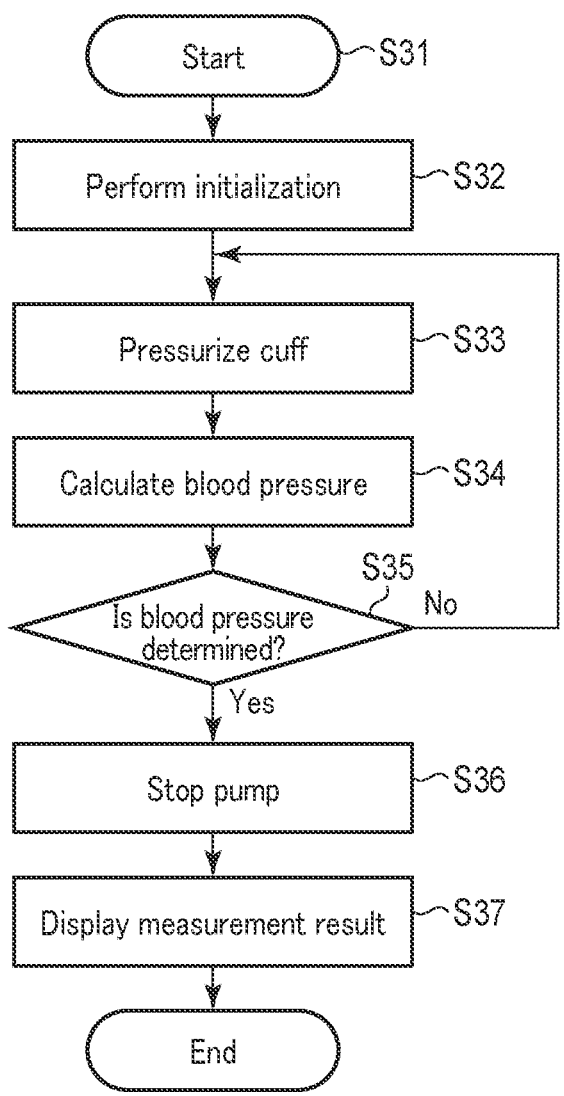
F I G. 10

PULSE TRANSIT TIME MEASURING APPARATUS AND BLOOD PRESSURE MEASURING APPARATUS

CROSS-REFERENCE TO RELATED APPLICATIONS

This application is a Continuation Application of PCT Application No. PCT/JP2019/006710, filed Feb. 22, 2019 and based upon and claiming the benefit of priority from Japanese Patent Application No. 2018-47031, filed Mar. 14, 2018, the entire contents of all of which are incorporated herein by reference.

FIELD

The present invention relates to a pulse transit time measuring apparatus that noninvasively measures a pulse transit time, and a blood pressure measuring apparatus that uses the pulse transit time measuring apparatus.

BACKGROUND

It is known that there is a correlation between blood pressure and a pulse transit time (PTT) which is a time required for a pulse wave to propagate between two points on an artery.

Patent Literature 1 discloses a blood pressure measuring apparatus that measures blood pressure using the above-described correlation. This blood pressure measuring apparatus calculates a pulse transmit time based on an output of an electrocardiogram (ECG) sensor and an output of a photoplethysmographic (PPG) sensor, and calculates a blood pressure value using the calculated pulse transit time and a relational expression representing the correlation. The ECG sensor is worn on a user's torso while the PPG sensor is worn on a user's ear.

CITATION LIST

Patent Literature

[Patent Literature 1] Japanese Patent No. 5984088

SUMMARY

In a blood pressure measuring apparatus disclosed in Patent Literature 1, a user needs to wear two devices, which is troublesome for the user.

The present invention has been made in view of the above circumstances, and an object is to provide a pulse transit time measuring apparatus and a blood pressure measuring apparatus that are easily worn by a user.

In order to achieve the object, the present invention adopts the following configurations.

A pulse transit time measuring apparatus according to one aspect includes a belt unit configured to be wrapped around a measurement site of a user, an electrocardiogram acquisition unit including a plurality of electrodes provided at the belt unit, the electrocardiogram acquisition unit being configured to acquire an electrocardiogram of the user by using the plurality of electrodes, a pulse wave signal acquisition unit including a pulse wave sensor provided at the belt unit, the pulse wave signal acquisition unit being configured to acquire a pulse wave signal representing a pulse wave of the user by using the pulse wave sensor, and a pulse transit time calculation unit configured to calculate a pulse transit time based on a time difference between a waveform characteristic point of the electrocardiogram and a waveform characteristic point of the pulse wave signal.

In the above-described configuration, both the electrodes and the pulse wave sensor are provided in the belt unit. Accordingly, the electrodes and the pulse wave sensor can be attached to the user by wrapping the belt unit around the user. Thus, the user easily wear the apparatus. Further, the pulse transit time is calculated based on the time difference between the waveform characteristic point of the electrocardiogram and the waveform characteristic point of the pulse wave signal for the measurement site. In this case, the pulse transit time corresponds to a time required for the pulse wave to propagate a long distance from the heart to the measurement site, and has a larger value than when the pulse transit time is measured between two points in the measurement site. In other words, a long pulse wave propagation distance is secured. Therefore, the pulse transit time is less affected by an error caused at the time of calculating the time difference between the waveform characteristic point of the electrocardiogram and that of the pulse wave signal, and the pulse transit time can be accurately measured.

In one aspect, the pulse wave sensor may be arranged at a part, in the belt unit, located on a peripheral side in a state where the belt unit is wrapped around the measurement site of the user. With this configuration, a longer pulse wave propagation distance is secured, and the pulse transit time can be measured more accurately.

In one aspect, the plurality of electrodes may be arranged at a part, in the belt unit, located on a central side in a state where the belt unit is wrapped around the measurement site of the user. With this configuration, it is possible to acquire a signal representing the electrical activity of the heart at a higher signal-to-noise ratio (SN ratio), and it is possible to more accurately detect a time of the waveform characteristic point in the electrocardiogram. As a result, the pulse transit time can be measured more accurately.

In one aspect, the plurality of electrodes may be at least four electrodes, and the electrocardiogram acquisition unit may be configured to acquire a first potential difference between two first electrodes of the plurality of electrodes, acquire a second potential difference between two second electrodes of the plurality of electrodes, the two second electrodes being different from the two first electrodes, acquire a third potential difference being a difference between the first potential different and the second potential difference, and generate the electrocardiogram based on the third potential difference.

In the above-described configuration, the first potential difference may be affected by a body motion noise caused by body motion of the user. Since the second potential difference is also affected by a body motion noise of an equivalent level, the body motion noise can be removed or reduced by calculating the difference between the first potential difference and the second potential difference. It is possible to acquire an electrocardiogram with reduced body motion noise or from which a body motion noise has been removed, and it is possible to more accurately detect a time of the waveform characteristic point in the electrocardiogram. As a result, the pulse transit time can be measured more accurately.

In one aspect, the pulse transit time measuring apparatus may further includes a determination unit configured to determine, based on the pulse transit time, whether a condition in which measurement of blood pressure of the user is recommended is satisfied, and an instruction unit configured to output information giving an instruction to execute blood pressure measurement in response to the determination unit determining that the condition has been satisfied.

In the above-described configuration, when the condition is satisfied, for example, a message prompting execution of blood pressure measurement is presented to the user. Therefore, the blood pressure measurement is executed in a situation where the blood pressure measurement is recommended, for example, when the blood pressure rapidly increases.

In one aspect, the measurement site may be an upper arm. With this configuration, the pulse transit time measuring apparatus can be worn under clothes, thus can be made inconspicuous.

A blood pressure measuring apparatus according to one aspect includes the above-described pulse transit time measuring apparatus, and a blood pressure value calculation unit configured to calculate a blood pressure value based on the calculated pulse transit time.

According to the above-described configuration, it is possible to perform, by a single device, blood pressure measurement based on the pulse transit time (continuous blood pressure measurement for obtaining a blood pressure value for each heartbeat).

A blood pressure measuring apparatus according to one aspect includes the above-described pulse transit time measuring apparatus, a first blood pressure value calculation unit configured to calculate a first blood pressure value based on the calculated pulse transit time and a blood pressure calculation formula, a pressing cuff provided at the belt unit, a fluid supply unit configured to supply fluid to the pressing cuff, a pressure sensor configured to detect a pressure in the pressing cuff, a second blood pressure value calculation unit configured to calculate a second blood pressure value based on an output signal of the pressure sensor, and a calibration unit configured to calibrate the blood pressure calculation formula based on the pulse transit time obtained by the pulse transit time measuring apparatus and the second blood pressure value calculated by the second blood pressure value calculation unit.

In the above-described configuration, it is possible to perform, by a single device, blood pressure measurement based on the pulse transit time, cuff-type blood pressure measurement, which is more accurate, and calibration of the blood pressure calculation formula.

Advantageous Effects of Invention

According to the present invention, it is possible to provide a pulse transit time measuring apparatus and a blood pressure measuring apparatus that are easily worn by a user.

BRIEF DESCRIPTION OF THE DRAWINGS

FIG. 5 is a block diagram illustrating a hardware configuration of a control system of the blood pressure measuring apparatus shown in FIG. 1;

FIG. 10 is a flowchart illustrating an operation in which the blood pressure measuring apparatus shown in FIG. 1 performs blood pressure measurement by the oscillometric method;

DETAILED DESCRIPTION

Hereinafter, embodiments of the present invention will be described with reference to the drawings.

Application Example

Figure 1:
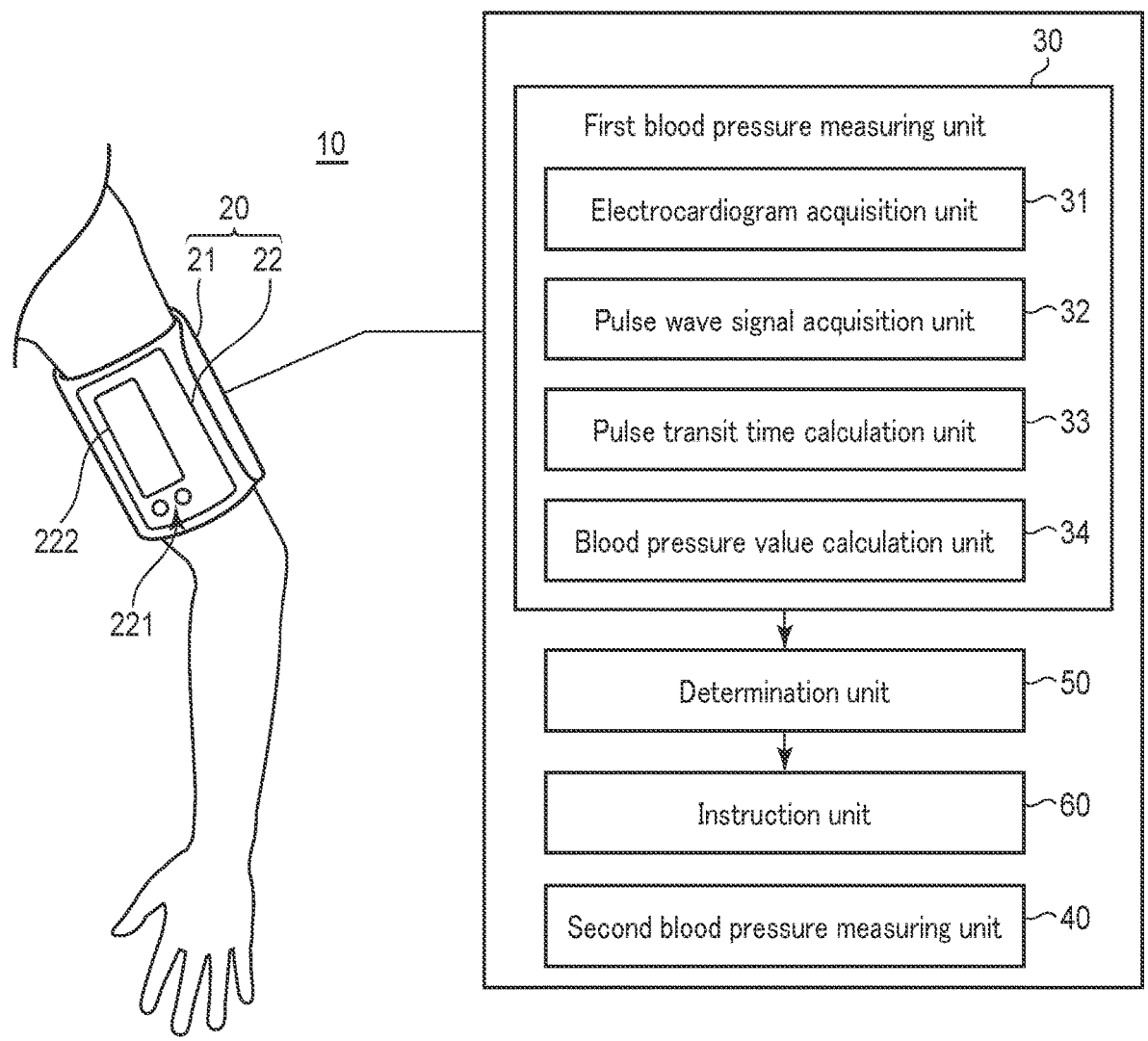
FIG. 1 illustrates a blood pressure measuring apparatus according to an embodiment.

With reference to FIG. 1, an example of a scene to which the present invention is applied will be described. FIG. 1 illustrates a blood pressure measuring apparatus 10 according to an embodiment. The blood pressure measuring apparatus 10 is a wearable device, and is configured to be worn on an upper arm of a user corresponding to a measurement site of the user. The blood pressure measuring apparatus 10 includes a belt unit 20, a first blood pressure measuring unit 30, a second blood pressure measuring unit 40, a determination unit 50, and an instruction unit 60.

The belt unit 20 includes a belt 21 and a body 22. The belt 21 indicates a belt-shaped member worn around an upper arm, and may be referred to by another name such as a band or a cuff. The belt 21 has an inner peripheral surface and an outer peripheral surface. The inner peripheral surface is a surface that comes into contact with the upper arm of the user in a state where the blood pressure measuring apparatus 10 is worn by the user (hereinafter simply referred to as a "worn state"), and the outer peripheral surface is a surface on the opposite side of the inner peripheral surface.

The body 22 is attached to the belt 21. The body 22 accommodates components such as an operation unit 221 and a display unit 222 together with a controller 501 (shown in FIG. 5) which will be described later. The operation unit 221 is an input device that allows a user to input an instruction to the blood pressure measuring apparatus 10. In the example of FIG. 1, the operation unit 221 includes a plurality of push buttons. The display unit 222 is a display device that displays information such as a message prompting execution of blood pressure measurement and a blood pressure measurement result. As the display device, for example, a liquid crystal display (LCD) or an organic light emitting diode (OLED) display may be used. A touch screen serving as both a display device and an input device may be used. The body 22 may be provided with a sound emitting body such as a speaker or a piezoelectric sounder. The body 22 may be provided with a microphone so that the user can input instructions by voice.

The first blood pressure measuring unit 30 noninvasively measures a pulse transit time of the user, and calculates a blood pressure value based on the measured pulse transit time. The first blood pressure measuring unit 30 can perform continuous blood pressure measurement for obtaining a blood pressure value for each heartbeat. The second blood pressure measuring unit 40 performs blood pressure measurement by a method different from that of the first blood pressure measuring unit 30. The second blood pressure measuring unit 40 is based on, for example, the oscillometric method or the Korotkoff method, and performs blood pressure measurement at a specific timing, for example, in response to an operation by the user. The second blood pressure measuring unit 40 cannot perform continuous blood pressure measurement, but can measure blood pressure more accurately than the first blood pressure measuring unit 30.

The first blood pressure measuring unit 30 includes an electrocardiogram acquisition unit 31, a pulse wave signal acquisition unit 32, a pulse transit time calculation unit 33, and a blood pressure value calculation unit 34.

The electrocardiogram acquisition unit 31 includes a plurality of electrodes, and acquires an electrocardiogram (ECG) of the user using these electrodes. An electrocardiogram represents an electrical activity of a heart. The electrodes are provided at the belt unit 20. For example, the electrodes are disposed on the inner peripheral surface of the belt 21, so that the electrodes come into contact with a skin of the upper arm of the user in the worn state.

The pulse wave signal acquisition unit 32 includes a pulse wave sensor, and acquires a pulse wave signal representing a user's pulse wave by using the pulse wave sensor. The pulse wave sensor is provided at the belt unit 20. For example, the pulse wave sensor is disposed on the inner peripheral surface of the belt 21 so that the pulse wave sensor comes in contact with the skin of the upper arm of the user in the worn state. Some types of pulse wave sensors, such as a pulse wave sensor based on a radio wave method described later, do not need to be in contact with the skin of the upper arm of the user in the worn state.

The pulse transit time calculation unit 33 calculates a pulse transit time based on a time difference between a waveform characteristic point of the electrocardiogram acquired by the electrocardiogram acquisition unit 31 and a waveform characteristic point of the pulse wave signal acquired by the pulse wave signal acquisition unit 32. For example, the pulse transit time calculation unit 33 calculates the time difference between the waveform characteristic point of the electrocardiogram and the waveform characteristic point of the pulse wave signal, and outputs the calculated time difference as the pulse transit time. In the present embodiment, the pulse transit time corresponds to the time required for the pulse wave to propagate through the artery from the heart to the upper arm (specifically, a position where the pulse wave sensor is disposed).

The blood pressure value calculation unit 34 calculates a blood pressure value based on the pulse transit time calculated by the pulse transit time calculation unit 33 and a blood pressure calculation formula. The blood pressure calculation formula is a relational expression representing a correlation between the pulse transit time and the blood pressure. An example of the blood pressure calculation formula is shown below.

$$SPB = \frac{A_1}{PTT^2} + A_2 \quad (1)$$

Here, SBP represents systolic blood pressure, PTT represents pulse transit time, and $A_1$ and $A_2$ are parameters. The above-described correlation is different for each individual. Therefore, it is necessary to calibrate the blood pressure calculation formula for the user. Calibration of the blood pressure calculation formula (to be specific, determination of parameters $A_1$ and $A_2$) is performed based on the blood pressure value obtained by the second blood pressure measuring unit 40. The calibration of the blood pressure calculation formula will be described later.

The pulse transit time calculation unit 33 can calculate the pulse transit time for each heartbeat, and therefore, the blood pressure value calculation unit 34 can calculate the blood pressure value for each heartbeat.

The determination unit 50 monitors the blood pressure values continuously obtained by the first blood pressure measuring unit 30, and determines whether a condition in which measurement of the user's blood pressure is recommended is satisfied. For example, when a rapid blood pressure increase occurs, it is desired to execute accurate blood pressure measurement by the second blood pressure measuring unit 40. Thus, the condition is defined, for example, to detect occurrence of a rapid blood pressure increase.

In response to the determination by the determination unit 50 that the condition is satisfied, the instruction unit 60 outputs information giving an instruction to execute blood pressure measurement using the second blood pressure measuring unit 40. For example, the instruction unit 60 outputs a notification sound (for example, melody) through the sound emitting body and displays a message "Please perform blood pressure measurement" on the display unit 222. When the user presses a predetermined button in response to the instruction from the instruction unit 60, blood pressure measurement by the second blood pressure measuring unit 40 is executed. The blood pressure measurement by the second blood pressure measuring unit 40 will be described later.

As described above, in the blood pressure measuring apparatus 10, the belt unit 20 is provided with both the plurality of electrodes used to acquire the electrocardiogram and the pulse wave sensor used to acquire the pulse wave signal. Thus, the electrodes and the pulse wave sensor can be attached to the user by simply wrapping the belt unit 20 around the upper arm. Therefore, the user can easily wear the blood pressure measuring apparatus 10, and the user's feeling against wearing the same can be reduced.

Further, a time difference between a waveform characteristic point of the electrocardiogram and a waveform characteristic point of the pulse wave signal for the upper arm is calculated as a pulse transit time. The pulse transit time obtained by the blood pressure measuring apparatus 10 has a larger value than that when the pulse transit time is measured between two points in the upper arm. In other words, a longer pulse wave propagation distance is ensured. Therefore, the pulse transit time is less affected by an error caused at the time of calculating the time difference between the waveform characteristic point of the electrocardiogram and the waveform characteristic point of the pulse wave signal, and the pulse transit time can be accurately measured. As a result, the reliability of the blood pressure value obtained by the blood pressure measurement based on the pulse transit time is improved.

Hereinafter, the blood pressure measuring apparatus 10 will be described in more detail.

Configuration Example (Hardware Configuration)

With reference to FIGS. 2 to 6, an example of a hardware configuration of the blood pressure measuring apparatus 10 according to the present embodiment will be described.

Figure 2:
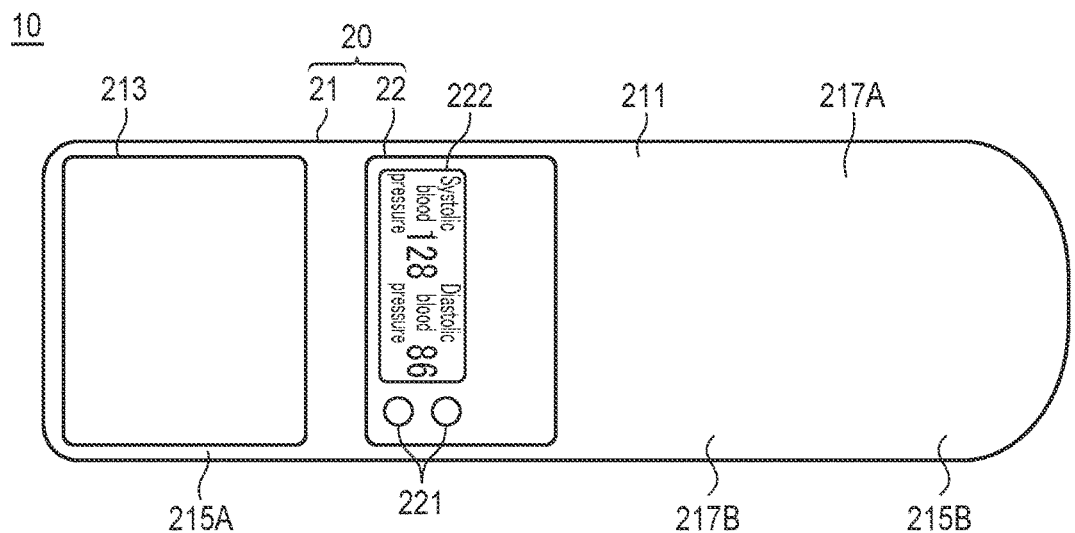
FIG. 2 illustrates an appearance of the blood pressure measuring apparatus shown in FIG. 1.
Figure 3:
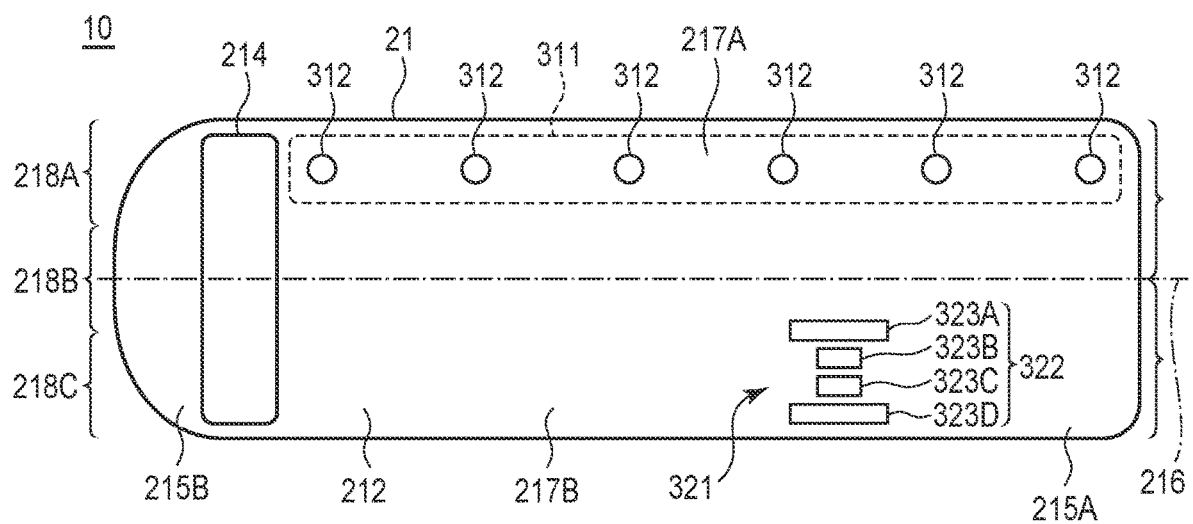
FIG. 3 illustrates an appearance of the blood pressure measuring apparatus shown in FIG. 1.
Figure 4:
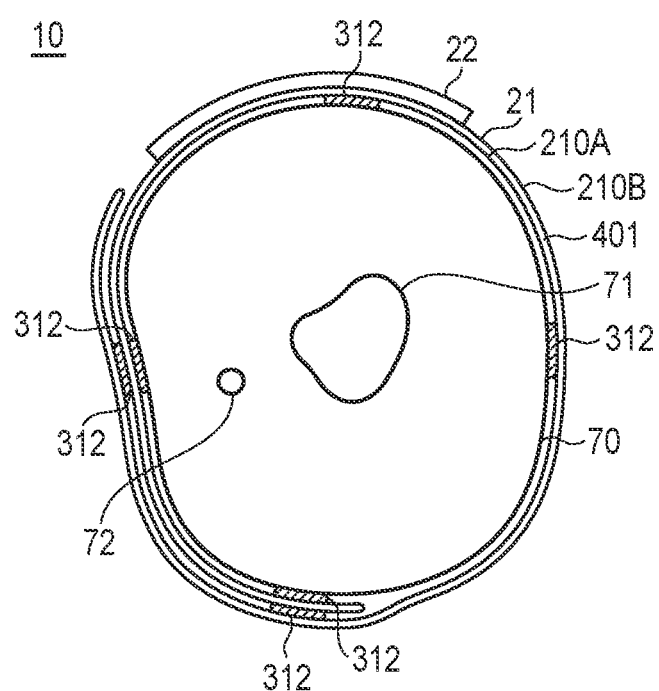
FIG. 4 illustrates a cross-section of the blood pressure measuring apparatus shown in FIG. 1.

FIGS. 2 and 3 are plan views illustrating an appearance of the blood pressure measuring apparatus 10. Specifically, FIG. 2 shows the blood pressure measuring apparatus 10 viewed from an outer peripheral surface 211 side of the belt 21 in a state where the belt 21 is unfolded, while FIG. 3 shows the blood pressure measuring apparatus 10 viewed from an inner peripheral surface 212 side of the belt 21 in a state where the belt 21 is unfolded. FIG. 4 shows a cross section of the blood pressure measuring apparatus 10 in a worn state.

The belt 21 includes an attachment member that allows the belt 21 to be attached to and detached from the upper arm. In the example shown in FIGS. 2 and 3, the attachment member is a hook-and-loop fastener including a loop surface 213 having a large number of loops, and a hook surface 214 having a plurality of hooks. The loop surface 213 is disposed on the outer peripheral surface 211 of the belt 21 at an end 215A in a longitudinal direction of the belt 21. The longitudinal direction corresponds to a circumferential direction of the upper arm in the worn state. The hook surface 214 is disposed on the inner peripheral surface 212 of the belt 21 at an end 215B in the longitudinal direction of the belt 21. The end portion 215B is opposed to the end portion 215A in the longitudinal direction of the belt 21. When the loop surface 213 and the hook surface 214 are pressed against each other, the loop surface 213 and the hook surface 214 bind. Furthermore, by pulling the loop surface 213 and the hook surface 214 away from each other, the loop surface 213 and the hook surface 214 are separated.

As shown in FIG. 3, an electrode group 311 for measuring an electrocardiogram is disposed on the inner peripheral surface 212 of the belt 21. In the example of FIG. 3, the electrode group 311 includes six electrodes 312 aligned at regular intervals in the longitudinal direction of the belt 21. The interval between the electrodes 312 is set to, for example, one fourth of a circumference of an upper arm of a user having a conceivable narrowest arm. In this arrangement, as illustrated in FIG. 4, for the user having the conceivable narrowest arm, four of the six electrodes 312 are in contact with the upper arm 70 in the worn state and are located at equal intervals on the circumference of the upper arm, while the remaining two electrodes 312 are in contact with the outer peripheral surface of the belt 111. In FIG. 4, a humerus 71 and a brachial artery 72 are shown. For a user with a conceivable thickest arm, all six electrodes 312 are in contact with the upper arm 70 in the worn state.

The number of electrodes 312 is not limited to six, and may be two to five, or seven or more. When two or three electrodes 312 are in contact with the upper arm, a good electrocardiogram may not obtained, depending on the worn state. If a good electrocardiogram cannot be obtained, it is necessary to have the user attach the blood pressure measuring apparatus 10 again by displaying a message on the display unit 222, etc. In order to avoid a situation where an electrocardiogram cannot be obtained, at least four electrodes 312 are desirably in contact with the upper arm in the worn state.

If the electrodes 312 are closer to the heart in the worn state, the signal representing the electrical activity of the heart obtained by means of the electrodes 312 has a larger value, i.e., a signal-to-noise ratio (SN ratio) becomes higher. Preferably, as illustrated in FIG. 3, the electrodes 312 are disposed on a central-side portion 217A of the belt 21. The central-side portion 217A is a portion located on a central side (shoulder side) with respect to a center line 216 in the worn state. More preferably, the electrodes 312 are disposed on a central-side end portion 218A of the belt 21. The central-side end portion 218A is an end portion located on the central side in the worn state, and the central-side end portion 218A has a width of, for example, one third of the entire width of the belt 21.

A sensor unit 322 of a pulse wave sensor 321 for measuring a pulse wave is further disposed on the inner peripheral surface 212 of the belt 21. In the example of FIG. 3, the sensor unit 322 includes a pair of electrodes 323A and 323D for supplying a current to the upper arm, and a pair of electrodes 323B and 323C for detecting a voltage. The electrodes 323A, 323B, 323C, and 323D are arranged in this order in the width direction of the belt 111. The width direction of the belt 111 is a direction along the brachial artery 72 in the worn state.

Further, as the sensor unit 322 is located farther from the heart in the worn state, the pulse wave propagation distance becomes longer, and the measured value of the pulse transit time becomes larger. Therefore, an error caused at the time of calculating the time difference between the waveform characteristic point of the electrocardiogram and the waveform characteristic point of the pulse wave signal becomes relatively small with respect to the pulse transit time, and the pulse transit time can be accurately measured. Preferably, the sensor unit 322 is disposed on a peripheral-side portion 217B of the belt 21. The peripheral-side portion 217B is a portion located on a peripheral side (elbow side) with respect to the center line 216 in the worn state. More preferably, the sensor unit 322 is disposed on a peripheral-side end portion 218C of the belt 21. The peripheral-side end portion 218C is an end portion located on the peripheral side in the worn state, and the peripheral-side end portion 218C has a width of, for example, one third of the entire width of the belt 21. A portion 218B between the central-side end portion 218A and the peripheral-side end portion 218C is referred to as an intermediate portion.

As shown in FIG. 4, the belt 21 includes an inner fabric 210A, an outer fabric 210B, and a pressing cuff 401 provided between the inner fabric 210A and the outer fabric 210B. The pressing cuff 401 is a belt-shaped body elongated in the longitudinal direction of the belt 21 so as to be able to surround the upper arm. For example, the pressing cuff 401 is configured as a fluid bag by opposing two stretchable polyurethane sheets in the thickness direction and welding peripheral parts thereof. The electrode group 311 and the sensor unit 322 are provided in the inner fabric 210A to be positioned between the pressing cuff 401 and the upper arm 70 in the worn state.

FIG. 5 illustrates an example of a hardware configuration of a control system of the blood pressure measuring apparatus 10 according to the present embodiment. In the example of FIG. 5, in addition to the operation unit 221 and the display unit 222 described above, a controller 501, a storage device 505, a battery 506, a switching circuit 313, a subtractor circuit 314, an analog front end (AFE) 315, a pressure sensor 402, a pump 403, a valve 404, an oscillation circuit 405, and a pump driving circuit 406 are mounted on the body 22. The pulse wave sensor 321 includes a current supply and voltage detection circuit 324 in addition to the above-described sensor unit 322. In this example, the current supply and voltage detection circuit 324 is mounted on the belt 21.

The controller 501 includes a central processing unit (CPU) 502, a random access memory (RAM) 503, and a read only memory (ROM) 504, and controls each component in accordance with information processing. The storage device 505 is, for example, an auxiliary storage device such as a hard disk drive (HDD) or a semiconductor memory (for example, a flash memory), and stores, in a non-volatile manner, programs (e.g., including a pulse transit time measurement program and a blood pressure measurement program) executed by the controller 501, setting data necessary for executing the programs, blood pressure measurement results, and the like. A storage medium included in the storage device 505 is a medium storing information of programs recorded thereon in an electronic, magnetic, optical, mechanical, or chemical manner so that the information of programs is readable by a computer, device or machine. Some or all of the programs may be stored in the ROM 504.

A battery 506 supplies power to components such as the controller 501. The battery 506 is, for example, a rechargeable battery.

Each of the electrodes 312 included in the electrode group 311 is connected to an input terminal of the switching circuit 313. Two output terminals of the switching circuit 313 are connected to two input terminals of the subtractor circuit 314, respectively. The switching circuit 313 receives a switch signal from the controller 501 and connects two electrodes 312 designated by the switch signal to the subtractor circuit 314. The subtractor circuit 314 subtracts the potential input from one input terminal from the potential input from the other input terminal. The subtractor circuit 314 outputs a potential difference signal representing a potential difference between the two connected electrodes 312 to the AFE 135. The subtractor circuit 314 is, for example, an instrumentation amplifier. The AFE 135 includes, for example, a low-pass filter (LPF), an amplifier, and an analog-to-digital converter. The potential difference signal is filtered by the LPF, amplified by the amplifier, and converted into a digital signal by the analog-to-digital converter. The potential difference signal converted into the digital signal is supplied to the controller 501. The controller 501 acquires, as an electrocardiogram, potential difference signals output from the AFE 315 in a time-series manner.

The current supply and voltage detection circuit 324 supplies a high-frequency constant current between the electrodes 323A and 323D. For example, the frequency of the current is 50 kHz, and the current value is 1 mA. The current supply and voltage detection circuit 324 detects a voltage between the electrodes 323B and 323C in a state where the electrodes 323A and 323D are supplied with the current, and generates a detection signal. The detection signal represents a change in an electrical impedance by pulse waves propagating through an artery portion facing the electrodes 323B and 323C. The current supply and voltage detection circuit 324 performs signal processing including rectification, amplification, filtering, and analog-to-digital conversion on the detection signal, and supplies the detection signal to the controller 501. The controller 501 acquires a detection signal output in a time-series manner from the current supply and voltage detection circuit 324 as a pulse wave signal.

The pressure sensor 402 is connected to the pressing cuff 401 via a pipe 407, while a pump 403 and a valve 404 are connected to the pressing cuff 401 via a pipe 408. The pipes 407 and 408 may be a single common pipe. The pump 403 is, for example, a piezoelectric pump, and supplies air as a fluid to the pressing cuff 401 through the pipe 408 in order to increase the pressure in the pressing cuff 401. The valve 404 is mounted on the pump 403, and is configured to be controlled to open and close in accordance with an operation state (on/off) of the pump 403. Specifically, when the pump 403 is turned on, the valve 404 is closed, and when the pump 403 is turned off, the valve 404 is opened. When the valve 404 is in an open state, the pressing cuff 401 communicates with the atmosphere, and the air in the pressing cuff 401 is discharged to the atmosphere. The valve 404 has a function of a check valve, and air does not flow backward. The pump driving circuit 406 drives the pump 403 based on the control signal received from the controller 501.

The pressure sensor 402 detects a pressure in the pressing cuff 401 (also referred to as a cuff pressure), and generates an electrical signal representing the cuff pressure. The cuff pressure is, for example, a pressure based on atmospheric pressure. The pressure sensor 402 is, for example, a piezoresistive pressure sensor. The oscillation circuit 405 oscillates based on the electric signal from the pressure sensor 402, and outputs the frequency signal having a frequency corresponding to the electric signal to the controller 501. In this example, the output of the pressure sensor 402 is used to control the pressure of the pressing cuff 401 and to calculate the blood pressure values (including systolic blood pressure and diastolic blood pressure) by an oscillometric method.

The pressing cuff 401 may be used to adjust a contact state between the electrode 312 or the sensor unit 322 of the pulse wave sensor 321 and the upper arm. For example, when the blood pressure measurement based on the pulse transit time is executed, the pressing cuff 401 is maintained in a state in which a certain amount of air is stored. Thus, the electrode 312 and the sensor unit 322 of the pulse wave sensor 321 are reliably brought into contact with the upper arm.

In the examples illustrated in FIGS. 2 to 5, the electrode group 311, the switching circuit 313, the subtractor circuit 314, and the AFE 315 correspond to the electrocardiogram acquisition unit 31 of the first blood pressure measuring unit 30 shown in FIG. 1, and the pulse wave sensor 321 (the electrodes 323 and the current supply and voltage detection circuit 324) corresponds to the pulse wave signal acquisition unit 32 of the first blood pressure measuring unit 30. The pressing cuff 401, the pressure sensor 402, the pump 403, the valve 404, the oscillation circuit 405, the pump driving circuit 406, and the pipes 407 and 408 correspond to the second blood pressure measuring unit 40.

Regarding a specific hardware configuration of the blood pressure measuring apparatus 10, components may be omitted, replaced, or added as appropriate according to an embodiment. For example, the controller 501 may include a plurality of processors. The blood pressure measuring apparatus 10 may include a communication unit 507 for communicating with an external device such as a mobile terminal (for example, a smartphone) of a user. The communication unit 507 includes a wired communication module and/or a wireless communication module. As the wireless communication method, for example, Bluetooth (registered trademark), Bluetooth Low Energy (BLE), or the like can be employed.

(Software Configuration)

Figure 6:
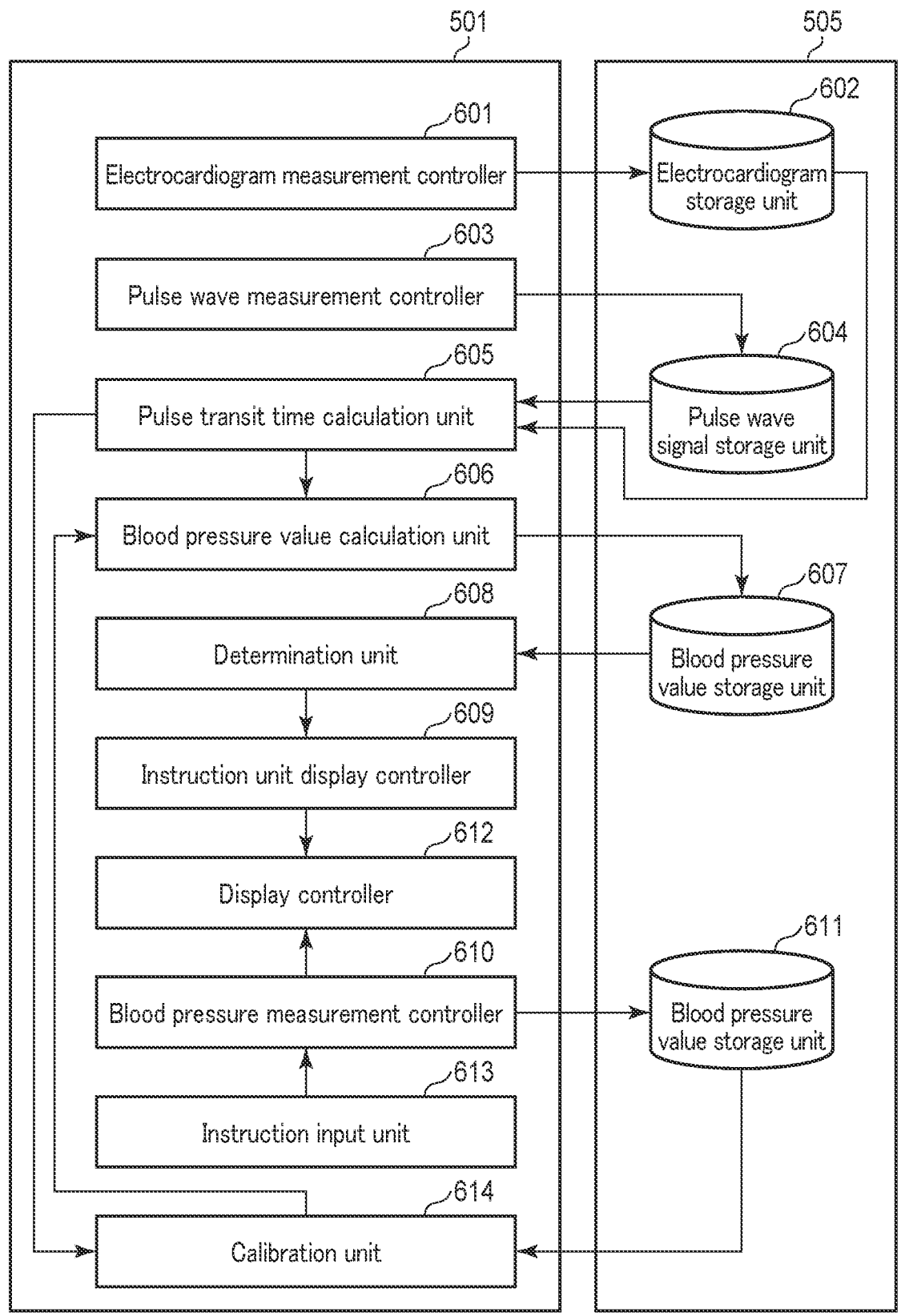
FIG. 6 is a block diagram illustrating a software configuration of the blood pressure measuring apparatus shown in FIG. 1.

With reference to FIG. 6, an example of a software configuration of the blood pressure measuring apparatus 10 according to the present embodiment will be described. FIG. 6 illustrates an example of a software configuration of the blood pressure measuring apparatus 10 according to the present embodiment. In the example illustrated in FIG. 6, the blood pressure measuring apparatus 10 includes an electrocardiogram measurement controller 601, an electrocardiogram storage unit 602, a pulse wave measurement controller 603, a pulse wave signal storage unit 604, a pulse transit time calculation unit 605, a blood pressure value calculation unit 606, a blood pressure value storage unit 607, a determination unit 608, an instruction unit 609, a blood pressure measurement controller 610, a blood pressure value storage unit 611, a display controller 612, an instruction input unit 613, and a calibration unit 614. The electrocardiogram measurement controller 601, the pulse wave measurement controller 603, the pulse transit time calculation unit 605, the blood pressure value calculation unit 606, the determination unit 608, the instruction unit 609, the blood pressure measurement controller 610, the display controller 612, the instruction input unit 613, and the calibration unit 614 perform the following processing by the controller 501 of the blood pressure measuring apparatus 10 executing a program stored in the storage device 505. When the controller 501 executes the program, the controller 501 loads the program onto the RAM 503. Then, the controller 501 interprets and executes the program loaded onto the RAM 503 by the CPU 502 to control each component. The electrocardiogram storage unit 602, the pulse wave signal storage unit 604, the blood pressure value storage unit 607, and the blood pressure value storage unit 611 are implemented by the storage device 505.

The electrocardiogram measurement controller 601 controls the switching circuit 313 to acquire an electrocardiogram. Specifically, the electrocardiogram measurement controller 601 generates a switch signal for selecting two electrodes 312 among the six electrodes 312, and supplies the switch signal to the switching circuit 313. The electrocardiogram measurement controller 601 acquires a potential difference signal obtained by using the selected two electrodes 312, and stores time-series data of the acquired potential difference signal in the electrocardiogram storage unit 602 as an electrocardiogram.

When the user wears the blood pressure measuring apparatus 10 on the upper arm, the electrocardiogram measurement controller 601 determines an electrode pair optimal to acquire an electrocardiogram. For example, the electrocardiogram measurement controller 601 acquires an electrocardiogram for each of all electrode pairs, and determines an electrode pair that provides an electrocardiogram having the largest R wave amplitude as an optimal electrode pair. Thereafter, the electrocardiogram measurement controller 601 measures the electrocardiogram using the optimal electrode pair.

The pulse wave measurement controller 603 controls the current supply and voltage detection circuit 324 to acquire a pulse wave signal. Specifically, the pulse-wave measurement controller 603 instructs the current supply and voltage detection circuit 324 to apply a current between the electrodes 323A and 323D, and acquires a detection signal indicating a voltage between the electrodes 323B and 323C detected in a state where the current flows between the electrodes 323A and 323D. The pulse wave measurement controller 603 stores time-series data of the detection signal as a pulse wave signal in the pulse wave signal storage unit 604.

Figure 7:
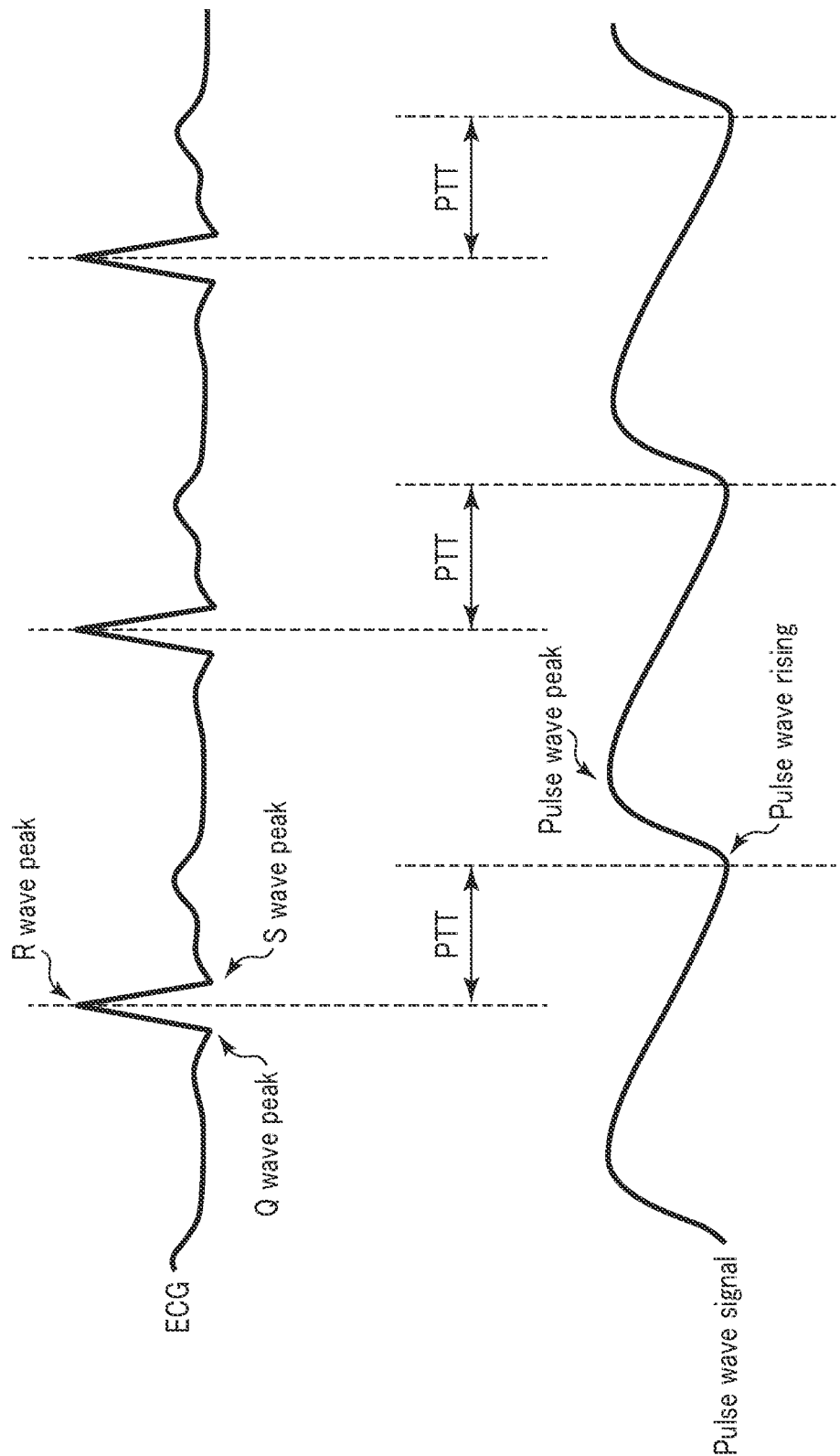
FIG. 7 is a diagram illustrating a method of calculating a pulse transit time by a pulse transit time calculation unit shown in FIG. 6.

The pulse transit time calculation unit 605 reads an electrocardiogram from the electrocardiogram storage unit 602, reads a pulse wave signal from the pulse wave signal storage unit 604, and calculates a pulse transit time based on a time difference between a waveform characteristic point of the electrocardiogram and a waveform characteristic point of the pulse wave signal. For example, as shown in FIG. 7, the pulse transit time calculation unit 605 detects a time (time point) of a peak point corresponding to an R wave from the electrocardiogram, detects a time (time point) of a rising point from the pulse wave signal, and calculates a difference obtained by subtracting the time of the peak point from the time of the rising point as a pulse transit time.

The pulse transit time calculation unit 605 may correct the time difference based on a pre-ejection period (PEP) and output the corrected time difference as the pulse transit time. For example, assuming that the pre-ejection period is constant, the pulse transit time calculation unit 605 may calculate the pulse transit time by subtracting a predetermined value from the time difference.

The peak point corresponding to the R wave is an example of the waveform characteristic point of the electrocardiogram. The waveform characteristic point of the electrocardiogram may be a peak point corresponding to a Q wave, or a peak point corresponding to an S wave. Since the R wave appears as a distinct peak as compared to the Q wave or the S wave, the time of the R-wave peak point can be specified more accurately. Therefore, preferably the R-wave peak point is used as the waveform characteristic point of the electrocardiogram. The rising point is an example of the waveform characteristic point of the pulse wave signal. The waveform characteristic point of the pulse wave signal may be a peak point. Since the pulse wave signal changes slightly with time, an error is likely to occur when the time of the waveform characteristic point is specified in the pulse wave signal.

Referring to FIG. 6, the blood pressure value calculation unit 606 calculates a blood pressure value based on the pulse transit time calculated by the pulse transit time calculation unit 605 and the blood pressure calculation formula. The blood pressure value calculation unit 606 uses, for example, the above-described formula (1) as a blood pressure calculation formula. The blood pressure value calculation unit 606 stores the calculated blood pressure value in the blood pressure value storage unit 607 in association with time information.

The blood pressure calculation formula is not limited to the above formula (1). The blood pressure calculation formula may be, for example, the following formula.

$$SBP = \frac{B_1}{PTT^2} + \frac{B_2}{PTT} + B_3 \times PTT + B_4 \quad (2)$$

where $B_1$, $B_2$, $B_3$, and $B_4$ are parameters.

The determination unit 608 corresponds to the determination unit 50 shown in FIG. 1. Based on the pulse transit time calculated by the pulse transit time calculation unit 605, the determination unit 608 determines whether a condition in which measurement of the blood pressure of the user is recommended is satisfied. In one example, the determination unit 608 determines whether a blood pressure change rate exceeds a threshold. The blood pressure change rate is, for example, an amount of change of the blood pressure value in a unit time. Specifically, the determination unit 608 determines whether a difference obtained by subtracting the blood pressure value before the unit time from the latest blood pressure value exceeds a threshold. If the latest systolic blood pressure value is $SBP_0$, the value of the systolic blood pressure before the unit time is $SBP_1$, and the threshold value is $V_{th}$, the determination unit 608 determines whether the conditional formula of $SBP_0 - SBP_1 > V_{th}$ is satisfied. The unit time is, for example, 30 seconds, and the threshold value is, for example, 20 [mmHg]. If the latest pulse transit time value is $PTT_0$ and value of the pulse transit time before the unit time is $PTT_1$, when the above conditional formula is modified using the formula (1), $$A_1\left(\frac{1}{PTT_0^2} - \frac{1}{PTT_1^2}\right) > V_{th}.$$

That is, the determination unit 608 may use the pulse transit time itself, or may use the blood pressure value calculated based on the pulse transit time. The determination unit 608 may determine whether a difference obtained by subtracting a blood pressure value before a predetermined heart rate (for example, before 30 beats) from the latest blood pressure value exceeds a threshold. In another example, the determination unit 608 determines whether the latest systolic blood pressure value exceeds a threshold (for example, 150 [mmHg]). The threshold may be fixed or variable. For example, the higher the average blood pressure of the user is, the higher the threshold value is set.

The instruction unit 609 corresponds to the instruction unit 60 shown in FIG. 1. In response to determination by determination unit 608 that the condition is satisfied, the instruction unit 609 outputs information giving an instruction to execute blood pressure measurement. For example, the instruction unit 609 gives an instruction signal to a display controller 612 to display a message prompting execution of blood pressure measurement on the display unit 222. Further, the instruction unit 609 outputs a control signal for controlling a driving circuit that drives the sound emitting body to generate a notification sound. The instruction unit 609 may transmit an instruction signal to the mobile terminal of the user via the communication unit 507, thereby prompting the user to perform blood pressure measurement through the mobile terminal.

The instruction input unit 613 receives an instruction that is input by the user using the operation unit 221. For example, when an operation to give an instruction to execute blood pressure measurement is made, the instruction input unit 613 gives an instruction to the blood pressure measurement controller 610 for starting blood pressure measurement.

The blood pressure measurement controller 610 controls the pump driving circuit 406 to execute blood pressure measurement. Upon receipt of the instruction for starting blood pressure measurement from the instruction input unit 613, the blood pressure measurement controller 610 drives the pump 403 via the pump driving circuit 406. Thereby, supply of air to the pressing cuff 401 is started. The pressing cuff 401 inflates, thereby compressing the user's upper arm. The blood pressure measurement controller 610 monitors the cuff pressure using the pressure sensor 402. The blood pressure measurement controller 610 calculates a blood pressure value by the oscillometric method based on a pressure signal output from the pressure sensor 402 in a pressurization process of supplying air to the pressing cuff 401. A blood pressure value includes, but is not limited to, systolic blood pressure (SBP) and diastolic blood pressure (DBP). The blood pressure measurement controller 610 stores the calculated blood pressure value in the blood pressure value storage unit 611 in association with the time information. The blood pressure measurement controller 610 can calculate the pulse rate simultaneously with the blood pressure value. When the calculation of the blood pressure value is completed, the blood pressure measurement controller 610 stops the pump 403 via the pump driving circuit 406. Thus, air is exhausted from the pressing cuff 401 through the valve 404.

The display controller 612 controls the display unit 222. For example, the display controller 612 receives an instruction signal from the instruction unit 609 and displays a message included in the instruction signal on the display unit 222. The display controller 612 also displays the blood pressure measurement result on the display unit 222 after the blood pressure measurement by the blood pressure measurement controller 610 is completed.

The calibration unit 614 calibrates the blood pressure calculation formula based on the pulse transit time obtained by the pulse transit time calculation unit 605 and the blood pressure value obtained by the blood pressure measurement controller 610. The correlation between the pulse transit time and the blood pressure value varies for each individual. Further, the correlation changes according to the state in which the blood pressure measuring apparatus 10 is worn on the upper arm of the user. For example, even for the same user, the correlation changes between when the blood pressure measuring apparatus 10 is disposed closer to the shoulder and when the blood pressure measuring apparatus 10 is disposed closer to the elbow. In order to reflect such a change in the correlation, the blood pressure calculation formula is calibrated. The calibration of the blood pressure calculation formula is executed, for example, when the user wears the blood pressure measuring apparatus 10. For example, the calibration unit 614 obtains a plurality of sets of the pulse transit time measurement results and the blood pressure measurement results, and determines parameters $A_1$ and $A_2$ based on the plurality of sets of the pulse transit time measurement results and the blood pressure measurement results. For determining parameters $A_1$ and $A_2$, the calibration unit 614 uses a fitting method such as a least squares method or a maximum likelihood method, for example.

The present embodiment describes an example in which all the functions of the blood pressure measuring apparatus 10 are realized by a general-purpose processor. However, some or all of the functions may be implemented by one or more dedicated processors.

Example of Operation (Selection of Electrode Pair Used for Acquiring Electrocardiogram)

When the user wears the blood pressure measuring apparatus 10, first, a process of selecting an electrode pair to be used for acquiring an electrocardiogram is executed. In this process, the controller 501 operates as the pulse wave measurement controller 603. Here, it is assumed that the electrode group 311 includes four electrodes 312, referred to as electrodes 312-1, 312-2, 312-3, and 312-4 to distinguish them from each other. The controller 501 supplies a switch signal for selecting the electrodes 312-1 and 312-2 to the switching circuit 313, and acquires an electrocardiogram using a pair of electrodes 312-1 and 312-2. Next, the controller 501 supplies a switch signal for selecting the electrodes 312-1 and 312-3 to the switching circuit 313, and acquires an electrocardiogram using a pair of electrodes 312-1 and 312-3. Similarly, the controller 501 acquires electrocardiograms using a pair of electrodes 312-1 and 312-4, a pair of electrodes 312-2 and 312-3, a pair of electrodes 312-2 and 312-4, and a pair of electrodes 312-3 and 312-4. The controller 501 determines an electrode pair from which an electrocardiogram having the largest R wave amplitude is obtained as an electrode pair used for acquiring an electrocardiogram.

(Calibration of Blood Pressure Calculation Formula Used for Blood Pressure Measurement Based on Pulse Transit Time)

Next, the blood pressure calculation formula is calibrated. In this process, the controller 501 operates as the calibration unit 614. If the number of parameters included in the blood pressure calculation formula is N, N or more sets of the pulse transit time measurement values and the blood pressure measurement values are required. The above blood pressure calculation formula (1) has two parameters $A_1$ and $A_2$. In this case, for example, the controller 501 acquires a set of the pulse transit time measurement value and the blood pressure measurement value when the user is at rest, then causes the user to exercise, and acquires a set of the pulse transit time measurement value and the blood pressure measurement value after the exercise. In this manner, two sets of the pulse transit time measurement values and the blood pressure measurement values are acquired. The controller 501 determines parameters $A_1$ and $A_2$ based on the acquired two sets of the pulse transit time measurement values and the blood pressure measurement values. After the calibration is completed, the blood pressure measurement based on the pulse transit time can be executed.

(Blood Pressure Measurement Based on Pulse Transit Time)

Figure 8:
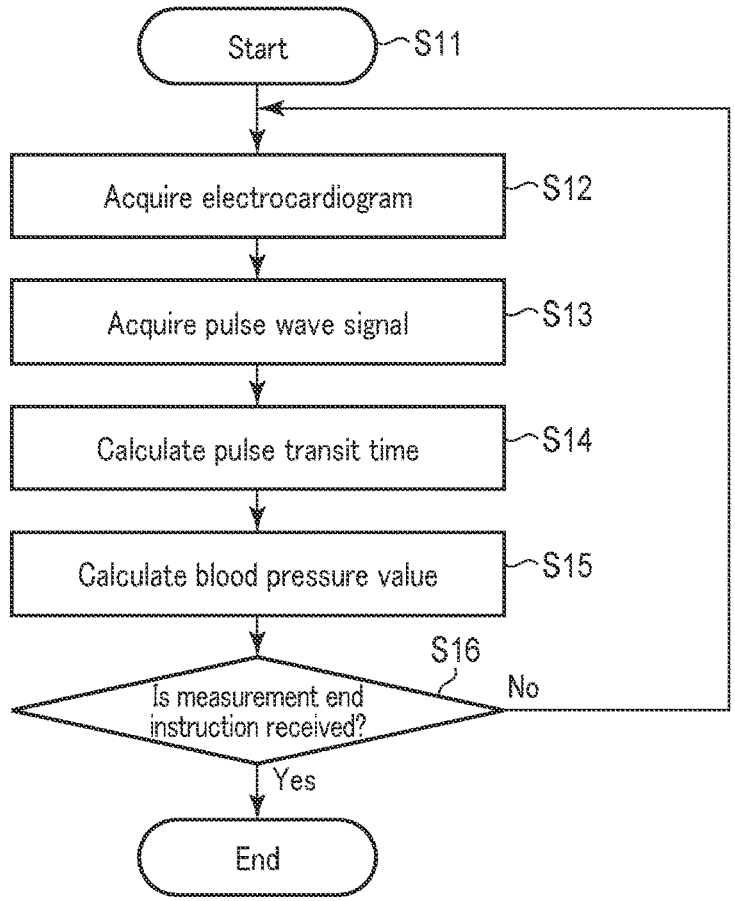
FIG. 8 is a flowchart illustrating an operation in which the blood pressure measuring apparatus shown in FIG. 1 performs blood pressure measurement based on the pulse transit time.

FIG. 8 shows an operation flow when the blood pressure measuring apparatus 10 performs blood pressure measurement based on the pulse transit time.

In step S11 of FIG. 8, the controller 501 starts blood pressure measurement based on the pulse transit time. For example, the controller 501 receives, from the operation unit 221, an operation signal indicating that the user has given an instruction for starting the blood pressure measurement based on the pulse transit time, and in response thereto, starts the blood pressure measurement. Alternatively, the controller 501 may start blood pressure measurement based on the pulse transit time in response to the completion of the calibration of the blood pressure calculation formula.

In step S12, the controller 501 operates as the electrocardiogram measurement controller 601, and acquires an electrocardiogram using the two electrodes 312 determined in the above-described process. In step S13, the controller 501 operates as the pulse wave measurement controller 603 and acquires a pulse wave signal using the pulse wave sensor 321. The processing of step S11 and that of step S12 are executed in parallel.

In step S14, the controller 501 operates as the pulse transit time calculation unit 605, and calculates the time difference between the R-wave peak point of the electrocardiogram and the rising point of the pulse wave signal as the pulse transit time. In step S15, the controller 501 operates as the blood pressure value calculation unit 606, and calculates the blood pressure value from the pulse transit time calculated in step S14 using the above-described blood pressure calculation formula (1). The controller 501 records the calculated blood pressure value in the storage device 505 in association with time information.

In step S16, the controller 501 determines whether an operation signal, indicating that the user has given an instruction to end the blood pressure measurement based on the pulse transit time, has been received from the operation unit 221. The processes of steps S12 to S15 are repeated until the controller 501 receives the operation signal. Thereby, the blood pressure value for each heartbeat is recorded. Upon receiving the operation signal, the controller 501 ends the blood pressure measurement based on the pulse transit time.

According to the blood pressure measurement based on the pulse transit time, the blood pressure can be continuously measured over a long period of time in a state in which the physical burden on the user is reduced.

(Instruction of Execution of Blood Pressure Measurement by Oscillometric Method)

Figure 9:
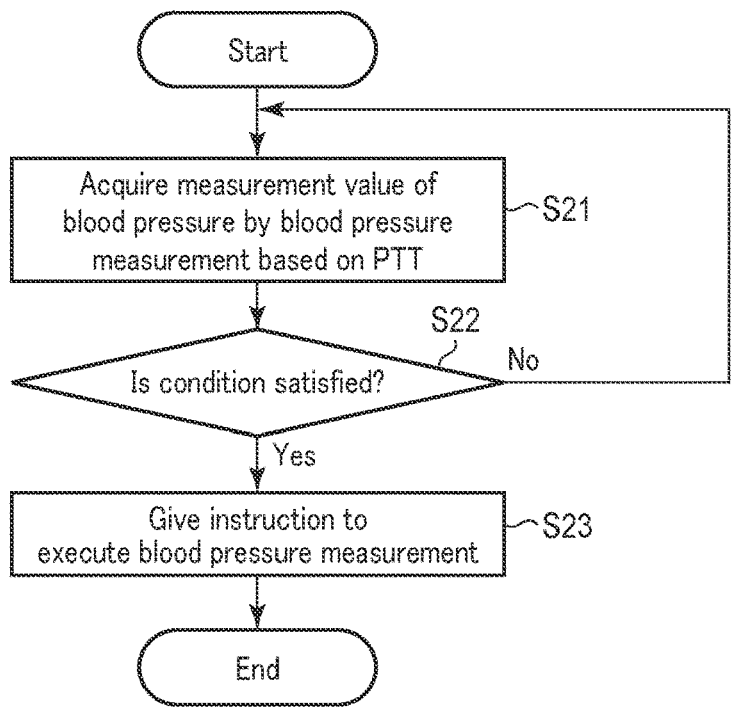
FIG. 9 is a flowchart illustrating an operation in which the blood pressure measuring apparatus shown in FIG. 1 gives an instruction to execute blood pressure measurement by an oscillometric method.

FIG. 9 illustrates an operation flow when the blood pressure measuring apparatus 10 gives an instruction for performing blood pressure measurement by the oscillometric method. The processing shown in FIG. 9 is executed during a period in which the blood pressure measurement based on the pulse transit time is executed.

In step S21 of FIG. 9, the controller 501 acquires the measurement value of the blood pressure by the blood pressure measurement based on the pulse transit time described with reference to FIG. 8.

In step S22, the controller 501 operates as the determination unit 608, and determines whether a condition in which measurement of the blood pressure of the user is recommended is satisfied based on the latest measurement value acquired in step S21. For example, the controller 501 determines whether the blood pressure value difference obtained by subtracting the blood pressure value before the unit time from the latest blood pressure value exceeds the threshold. When the blood pressure value difference is equal to or lower than the threshold value, the process returns to step S21, and the controller 501 acquires a next measurement value. When the blood pressure value difference exceeds the threshold, the process proceeds to step S23.

In step S23, the controller 501 operates as the instruction unit 609, and gives an instruction to execute the blood pressure measurement. For example, the controller 501 generates a notification sound using the sound emitting body, and displays a message prompting execution of blood pressure measurement on the display unit 222.

In this manner, the controller 501 instructs the user to execute blood pressure measurement by the oscillometric method when a situation comes in which accurate blood pressure measurement is recommended.

(Blood Pressure Measurement by Oscillometric Method)

FIG. 10 illustrates an operation flow when the blood pressure measuring apparatus 10 performs blood pressure measurement by the oscillometric method. In the oscillometric blood pressure measurement, the pressing cuff 401 is gradually pressurized and then depressurized. In such a pressurization or depressurization process, the pulse transit time cannot be accurately measured. Therefore, during the blood pressure measurement by the oscillometric method, the blood pressure measurement based on the pulse transit time shown in FIG. 8 may be temporarily stopped.

In step S31 of FIG. 10, the controller 501 starts blood pressure measurement by the oscillometric method. For example, the controller 501 receives, from the operation unit 221, an operation signal indicating that the user has given an instruction to execute blood pressure measurement by the oscillometric method, and in response thereto, starts blood pressure measurement.

In step S32, the controller 501 operates as the blood pressure measurement controller 610, and performs initialization for blood pressure measurement. For example, the controller 501 initializes the processing memory area. Then, the controller 501 stops the pump 403 via the pump driving circuit 406. Accordingly, the valve 404 is opened, and air in the pressing cuff 401 is discharged. The controller 501 sets a current output value of the pressure sensor 402 as a reference value.

Figure 11:
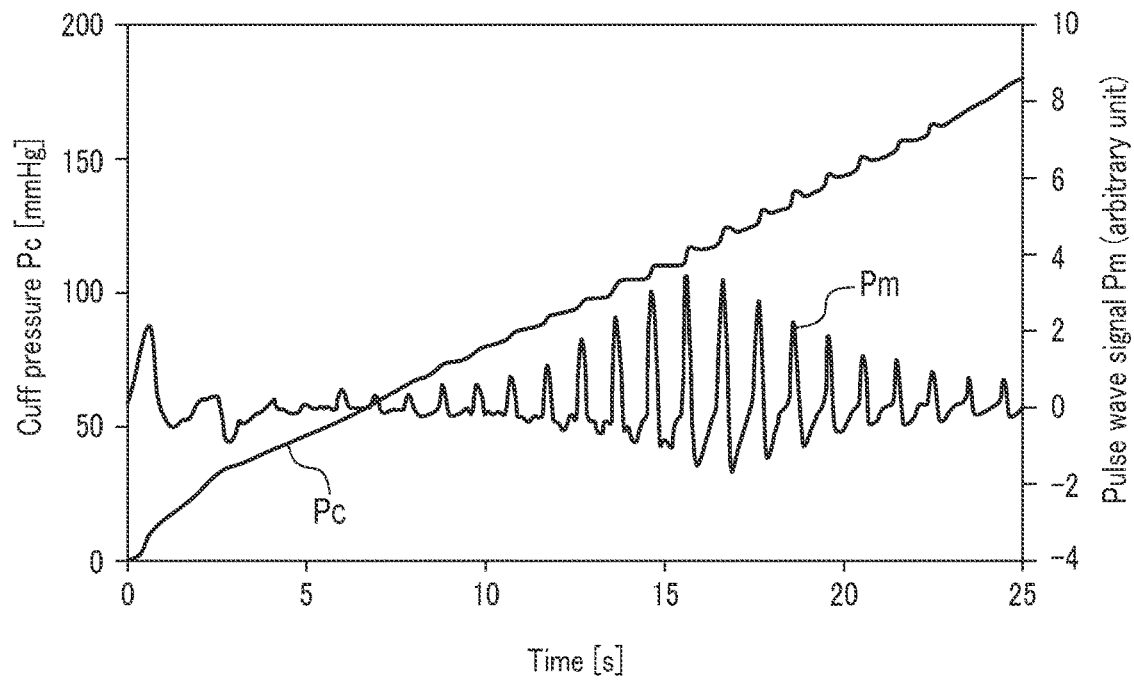
FIG. 11 shows changes in a cuff pressure and a pulse wave signal in blood pressure measurement by the oscillometric method.

In step S33, the controller 501 operates as the blood pressure measurement controller 610, and performs control to pressurize the pressing cuff 401. For example, the controller 501 drives the pump 403 via the pump driving circuit 406. Accordingly, the valve 404 is closed, and air is supplied to the pressing cuff 401. Thereby, the pressing cuff 401 inflates, and cuff pressure Pc gradually increases as shown in FIG. 11. The controller 501 monitors the cuff pressure Pc using the pressure sensor 402, and acquires pulse wave signal Pm representing a fluctuation component of an arterial volume.

In step S34, the controller 501 operates as the blood pressure measurement controller 610, and attempts to calculate a blood pressure value (including SBP and DBP) based on the pulse wave signal Pm acquired at this time. At this time, if the blood pressure value cannot be calculated (No in step S35) due to insufficient data, the processes of steps S33 and S34 are repeated unless the cuff pressure Pc reaches the upper limit pressure. The upper limit pressure is determined in advance from the viewpoint of safety. The upper limit pressure is, for example, 300 mmHg.

When the blood pressure value has been calculated (Yes in step S35), the process proceeds to step S36. In step S36, the controller 501 operates as the blood pressure measurement controller 610, and stops the pump 403 by the pump driving circuit 406. Accordingly, the valve 404 is opened, and air in the pressing cuff 401 is discharged.

In step S37, the controller 501 displays the blood pressure measurement result on the display unit 222, and records the result in the storage device 505.

The processing procedure shown in FIG. 8, FIG. 9, or FIG. 10 is an example, and the processing order or the content of each processing can be changed as appropriate. For example, in the blood pressure measurement by the oscillometric method, the calculation of the blood pressure value may be executed in a depressurization process in which air is discharged from the pressing cuff 401.

Advantageous Effect

As described above, in the blood pressure measuring apparatus 10 according to the present embodiment, both the electrode group 311 and the sensor unit 322 of the pulse wave sensor 321 are provided at the belt 21. Therefore, by simply wrapping the belt 21 around the upper arm, both the electrode group 311 and the pulse wave sensor 321 are attached to the user. Therefore, the user can easily wear the blood pressure measuring apparatus 10. Since the user only needs to wear one device, the user's feeling against wearing the blood pressure measuring apparatus 10 is reduced.

Further, since the pulse transit time is calculated based on the electrocardiogram and the pulse wave signal obtained for the upper arm, the pulse transit time can be obtained for a long distance from the heart to the upper arm. As a result, robustness against an error caused at the time of calculating the time difference between the waveform characteristic point of the electrocardiogram and the waveform characteristic point of the pulse wave signal is improved. Further, the electrode group 311 is disposed in the central-side portion 217A of the belt 21, and the sensor unit 322 of the pulse wave sensor 321 is disposed in the peripheral-side portion 217B of the belt 21. In this arrangement, a longer pulse wave propagation distance is ensured, and an electrocardiogram having a high SN ratio is acquired. This further improves the robustness. As a result, the pulse transit time can be accurately measured, and the reliability of the blood pressure value calculated based on the pulse transit time is improved.

The blood pressure calculation formula used in the first blood pressure measuring unit 30 is calibrated based on the blood pressure value obtained by the second blood pressure measuring unit 40. It is necessary to perform calibration based on a blood pressure value obtained by a measurement system different from the first blood pressure measuring unit 30. In the present embodiment, the second blood pressure measuring unit 40 is integrated with the first blood pressure measuring unit 30, and the blood pressure calculation formula is calibrated based on the blood pressure value obtained by the second blood pressure measuring unit 40. Thus, the blood pressure calculation formula can be calibrated by the blood pressure measuring apparatus 10 alone. Therefore, the blood pressure calculation formula can be easily calibrated.

In addition, it is determined whether a condition in which measurement of the blood pressure of the user is recommended is satisfied based on the result of the continuous blood pressure measurement by the first blood pressure measuring unit 30. When the condition is satisfied, the user is notified that the blood pressure measurement by the second blood pressure measuring unit 40 should be performed. Therefore, it is possible to cause the user to perform accurate blood pressure measurement in a situation in which blood pressure measurement is recommended.

Since the blood pressure measurement based on the pulse transit time and the blood pressure measurement by the oscillometric method can be performed by a single device, the user's convenience increases.

Since the blood pressure measuring apparatus 10 is worn on the upper arm, the blood pressure is measured at substantially the same height as the heart. Thus, it is not necessary to perform height correction on the obtained blood pressure measurement result. In addition, if the blood pressure measuring apparatus 10 is an upper arm type, the blood pressure measuring apparatus 10 can be hidden by the sleeves on clothes, and it is possible to make it inconspicuous that the blood pressure measuring apparatus 10 is worn.

(Modifications)

If an electrode group for measuring an electrocardiogram includes four or more electrodes, two of the electrodes, other than the two electrodes used for measuring an optimal electrocardiogram, may be used to remove or reduce body motion noise from the electrocardiogram. The body motion noise is noise caused by a body motion of the user. It is difficult to effectively reduce body motion noise with a filter such as a low-pass filter.

Figure 12:
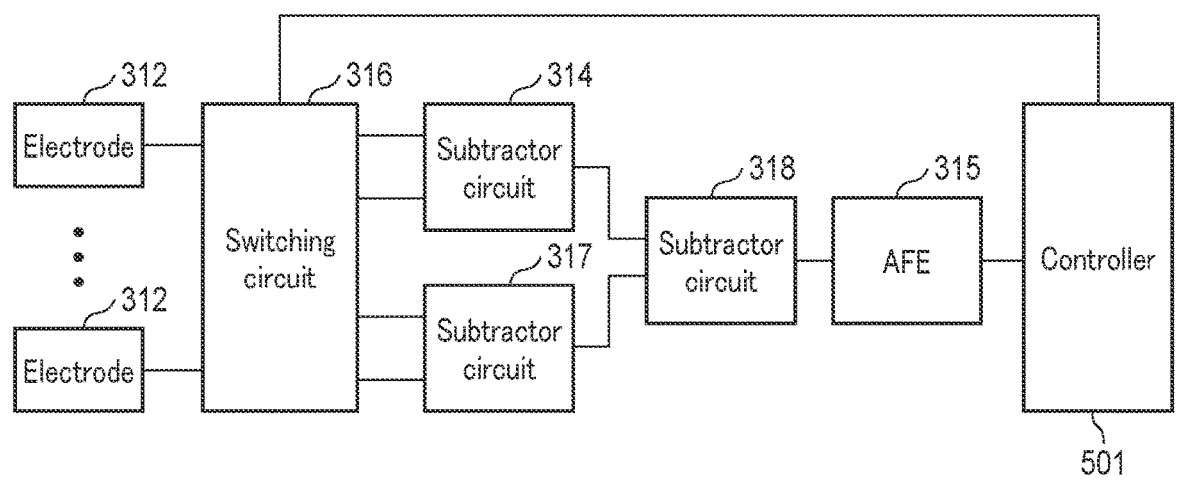
FIG. 12 is a block diagram illustrating a hardware configuration of an electrocardiogram acquisition unit according to an embodiment.

FIG. 12 illustrates an example of a hardware configuration of an electrocardiogram acquisition unit in a blood pressure measuring apparatus according to an embodiment. In FIG. 12, the same components as those shown in FIG. 5 are denoted by the same reference numerals, and a description thereof will be omitted. In the example of FIG. 12, electrodes 312 are connected to respective input terminals of a switching circuit 316. The switching circuit 316 is controlled by the controller 501. The controller 501 provides the switching circuit 316 with a first switch signal for selecting two electrodes to be used for electrocardiogram measurement, and a second switch signal for selecting two electrodes to be used for body motion noise reduction. The first and second output terminals of the switching circuit 316 are connected to a subtractor circuit 314, and the subtractor circuit 314 outputs a first potential difference signal representing a potential difference between two electrodes designated by the first switch signal to a subtractor circuit 318. The third and fourth output terminals of the switching circuit 316 are connected to a subtractor circuit 317, and the subtractor circuit 317 outputs a second potential difference signal representing a potential difference between two electrodes designated by the second switch signal to the subtractor circuit 318. The subtractor circuit 318 generates a third potential difference signal by subtracting the second potential difference signal from the first potential difference signal, and outputs the third potential difference signal to the AFE 135. Since the first potential difference signal and the second potential difference signal have substantially the same degree of body motion noise, the body motion noise can be removed or reduced.

In the above-described embodiment, the pulse wave sensor employs an impedance method for detecting a change in impedance associated with a change in the volume of an artery. The pulse wave sensor may employ another measurement method such as a photoelectric method, a piezoelectric method, or a radio wave method. In an embodiment employing the photoelectric method, the pulse wave sensor includes a light emitting element configured to emit light toward an artery passing through a measurement site, and a photodetector configured to detect reflected light or transmitted light of the light, and detects a change in light intensity associated with a change in the volume of the artery. In an embodiment employing the piezoelectric method, the pulse wave sensor includes a piezoelectric element provided in the belt so as to be in contact with the measurement site, and detects a change in a pressure associated with a change in the volume of the artery. In an embodiment employing the radio wave method, the pulse wave sensor includes a transmitting element configured to transmit a radio wave toward an artery passing through a measurement site and a receiving element configured to receive a reflected wave of the radio wave, and detects a phase shift between the transmitted wave and the reflected wave associated with a volume change of the artery.

The blood pressure measuring apparatus 10 may further include a pressing cuff for adjusting a contact state between the electrodes 312 and the upper arm, a pump for supplying air to the pressing cuff, a pump driving circuit for driving the pump, and a pressure sensor for detecting the pressure in the pressing cuff. The pressing cuff is provided in the central-side end portion 218A of the belt 21. In this case, the pressing cuff 401 is provided, for example, at an intermediate portion 218B of the belt 21.

The blood pressure measuring apparatus 10 may further include a pressing cuff for adjusting a contact state between the sensor unit 322 of the pulse wave sensor 321 and the upper arm, a pump for supplying air to the pressing cuff, a pump driving circuit for driving the pump, and a pressure sensor for detecting a pressure in the pressing cuff. The pressing cuff is provided at the peripheral-side end portion 218C of the belt 21. In this case, the pressing cuff 401 is provided, for example, at the intermediate portion 218B of the belt 21.

A part involved in the measurement of the pulse transit time may be realized as a single device. In one embodiment, there is provided a pulse transit time measuring apparatus including a belt unit 20, an electrocardiogram acquisition unit 31, a pulse wave signal acquisition unit 32, and a pulse transit time calculation unit 33. The pulse transit time measuring apparatus may further include a determination unit 50 and an instruction unit 60. The pulse transit time measuring apparatus may further include a pressing cuff, a pump, and a pump driving circuit to press the electrodes 312 and the pulse wave sensor 321 against the upper arm.

The blood pressure measuring apparatus 10 may not include the second blood pressure measuring unit 40. In an embodiment in which the blood pressure measuring apparatus 10 does not include the second blood pressure measuring unit 40, in order to calibrate the blood pressure calculation formula, it is necessary to input a blood pressure value obtained by measurement by another blood pressure monitor to the blood pressure measuring apparatus 10.

The measurement site is not limited to the upper arm, and may be another site such as a wrist, a thigh, or an ankle.

The present invention is not limited to the above-described embodiments as they are, and can be embodied by modifying the components without departing from the scope of the invention at the implementation stage. Further, various inventions can be formed by appropriately combining a plurality of components disclosed in the above embodiments. For example, some of the components may be deleted from each of the embodiments. In addition, the components between different embodiments may be combined as appropriate.

REFERENCE SIGNS LIST

10. Blood pressure measuring apparatus
20. Belt unit
21. Belt
22. Body
30. First blood pressure measuring unit
31. Electrocardiogram acquisition unit
32. Pulse wave signal acquisition unit
33. Pulse transit time calculation unit
34. Blood pressure value calculation unit
40. Second blood pressure measuring unit
50. Determination unit
60. Instruction unit
210A. Inner fabric
210B. Outer fabric
213. Loop surface
214. Hook surface
221. Operation unit
222. Display unit
311. Electrode group
312. Electrode
313. Switching circuit
314. Subtractor circuit
315. Analog front end
321. Pulse wave sensor
322. Sensor unit
323A to 323D. Electrode
324. Current supply and voltage detection circuit
401. Pressing cuff
402. Pressure sensor
403. Pump
404. Valve
405. Oscillation circuit
406. Pump driving circuit
407,408. Pipe
501. Controller
502. CPU
503. RAM
504. ROM
505. Storage device
506. Battery
507. Communication unit
601. Electrocardiogram measurement controller
602. Electrocardiogram storage unit
603. Pulse wave measurement controller
604. Pulse wave signal storage unit
605. Pulse transit time calculation unit 606. Blood pressure value calculation unit
607. Blood pressure value storage unit
608. Determination unit
609. Instruction unit
610. Blood pressure measurement controller
611. Blood pressure value storage unit
612. Display controller
613. Instruction input unit
614. Calibration unit

The invention claimed is:

1. A pulse transit time measuring apparatus comprising:
a belt unit configured to be wrapped around a measurement site of a user, the belt unit including a first surface and a second surface opposite to the first surface, the first surface being configured to be in contact with the measurement site of the user;
an electrocardiogram acquisition unit including at least four electrodes provided along one direction on the first surface of the belt unit, the at least four electrodes being in contact with the measurement site of the user in a state where the belt unit is wrapped around the measurement site of the user, the electrocardiogram acquisition unit being configured to acquire a first potential difference between two first electrodes of the at least four electrodes, acquire a second potential difference between two second electrodes of the at least four electrodes, the two second electrodes being different from the two first electrodes, subtract the second potential difference from the first potential difference to generate a third potential difference, and acquire an electrocardiogram of the user based on the third potential difference;
a pulse wave sensor provided at the belt unit, the pulse wave sensor being configured to detect a pulse wave of the user to acquire a pulse wave signal representing the pulse wave of the user; and
a processor configured to calculate a pulse transit time based on a time difference between a waveform characteristic point of the electrocardiogram and a waveform characteristic point of the pulse wave signal.

2. The pulse transit time measuring apparatus according to claim 1, wherein the pulse wave sensor is arranged at a part, in the belt unit, located on a peripheral side in a state where the belt unit is wrapped around the measurement site of the user.

3. The pulse transit time measuring apparatus according to claim 1, wherein the at least four electrodes are arranged at a part, in the belt unit, located on a central side in a state where the belt unit is wrapped around the measurement site of the user.

4. The pulse transit time measuring apparatus according to claim 1, wherein the processor is further configured to:
determine, based on the calculated pulse transit time, whether a condition in which measurement of blood pressure of the user is recommended is satisfied; and
output information giving an instruction to execute blood pressure measurement in response to determining that the condition has been satisfied.

5. The pulse transit time measuring apparatus according to claim 1, wherein the measurement site is an upper arm.

6. A blood pressure measuring apparatus comprising:
the pulse transit time measuring apparatus according to claim 1, wherein the processor is further configured to calculate a blood pressure value based on the calculated pulse transit time.

7. A blood pressure measuring apparatus comprising:
the pulse transit time measuring apparatus according to claim 1, wherein the processor is further configured to calculate a first blood pressure value based on the calculated pulse transit time and a blood pressure calculation formula;
a pressing cuff provided at the belt unit;
a fluid supply unit configured to supply fluid to the pressing cuff; and
a pressure sensor configured to detect a pressure in the pressing cuff,
wherein the processor is further configured to calculate a second blood pressure value based on an output signal of the pressure sensor, and calibrate the blood pressure calculation formula based on the pulse transit time obtained by the pulse transit time measuring apparatus and the calculated second blood pressure value.

8. The pulse transit time measuring apparatus according to claim 1, wherein the pulse wave sensor comprises:
a sensor unit comprising a first pair of first electrodes supplying a current to the user, and a second pair of electrodes for detecting the pulse wave signal.

* * * * *